United States Patent [19]

Daoud et al.

[11] Patent Number: 5,103,211
[45] Date of Patent: Apr. 7, 1992

[54] APPARATUS FOR DETECTING FLUID LINE OCCLUSION

[75] Inventors: Adib G. Daoud, San Diego; C. Russell Horres, Jr., Del Mar; Howard R. Everhart, San Diego, all of Calif.

[73] Assignee: IVAC Corporation, San Diego, Calif.

[21] Appl. No.: 610,385

[22] Filed: Nov. 6, 1990

Related U.S. Application Data

[63] Continuation-in-part of Ser. No. 430,809, Nov. 2, 1989, abandoned.

[51] Int. Cl.⁵ ............................................. G08B 21/00
[52] U.S. Cl. .................................. 340/608; 340/611; 417/63; 604/67; 128/DIG. 13
[58] Field of Search ............... 340/608, 603, 611; 417/63, 474, 479; 604/67; 128/DIG. 13

[56] References Cited

U.S. PATENT DOCUMENTS

| | | | |
|---|---|---|---|
| 4,277,226 | 7/1981 | Archibald | 55/381 |
| 4,278,085 | 7/1981 | Shim | 128/214 |
| 4,369,780 | 1/1983 | Sakai | 128/214 E |
| 4,373,525 | 2/1983 | Kobayashi | 128/214 |
| 4,530,696 | 7/1985 | Bisera et al. | 604/253 |
| 4,561,830 | 12/1985 | Bradley | 417/474 |
| 4,563,179 | 1/1986 | Sakai | 604/244 |
| 4,617,014 | 10/1986 | Cannon et al. | 604/67 |
| 4,653,987 | 3/1987 | Tsuji et al. | 417/360 |
| 4,690,673 | 9/1987 | Bloomquist | 604/67 |
| 4,702,675 | 10/1987 | Aldrovandi et al. | 417/63 |
| 4,747,828 | 5/1988 | Tseo | 604/67 |
| 4,758,228 | 7/1988 | Williams | 604/153 |
| 4,784,576 | 11/1988 | Bloom et al. | 417/63 |
| 4,784,577 | 11/1988 | Ritson et al. | 417/219 |
| 4,836,752 | 6/1989 | Burkett | 417/12 |

FOREIGN PATENT DOCUMENTS 0040592 11/1981 European Pat. Off. .
0283614 6/1987 European Pat. Off. .

Primary Examiner—Jin F. Ng
Assistant Examiner—Jeffery A. Hofsass
Attorney, Agent, or Firm—Fulwider Patton Lee & Utecht

[57] ABSTRACT

An apparatus and method for detecting pressure and occlusion in a fluid line is for use with a fluid line being operated upon by a positive displacement, peristaltic pump having several cam follower fingers pressing against the fluid line fluid through the line peristaltically. A sensor follower finger is mounted to the cam shaft of the pump among the other peristaltic fingers in order to cyclicly press against the fluid line and displace the fluid line by a predetermined amount as the cam shaft rotates. The sensor follower finger includes a strain gauge mounted on the sensor finger to generate a signal indicating the degree of force being applied by the sensor finger against the tubing, and a signal processor which receives this force signal and determines the pressure within the fluid line based upon the signal. The signal processor determines the existence of an occlusion based on the signal and provides an alarm if an occlusion is determined.

32 Claims, 4 Drawing Sheets

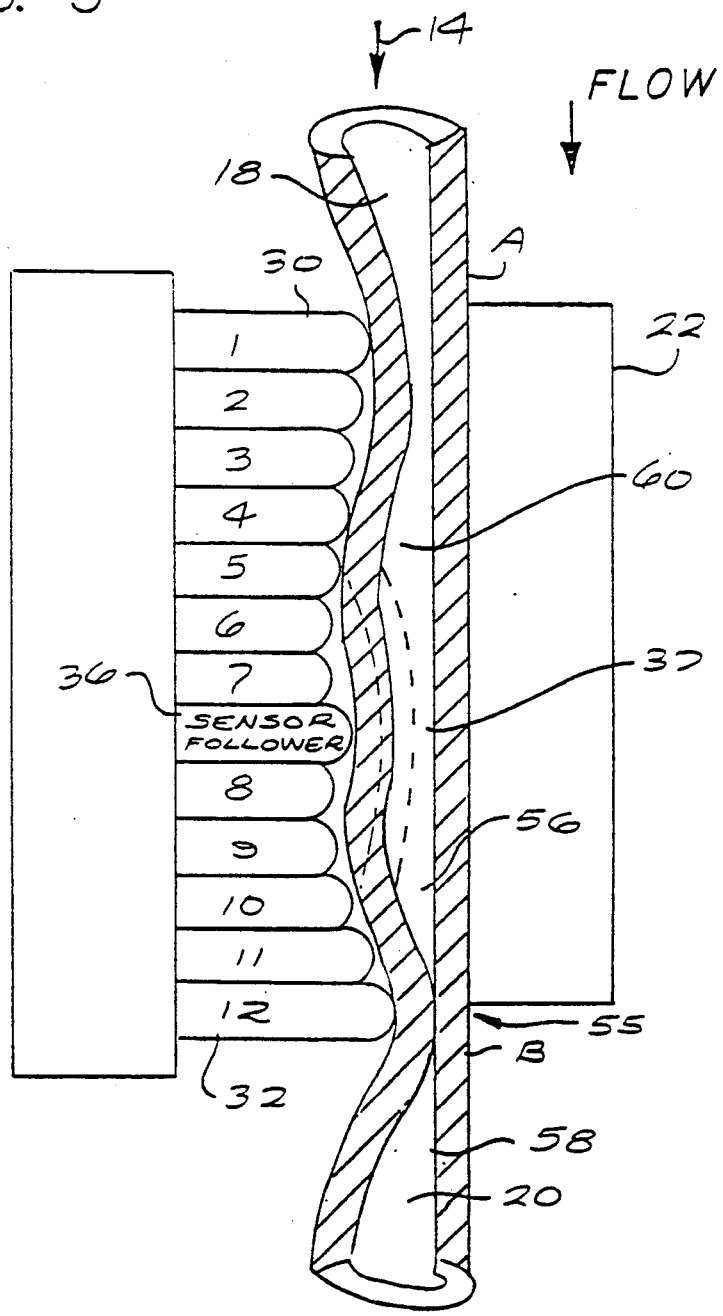

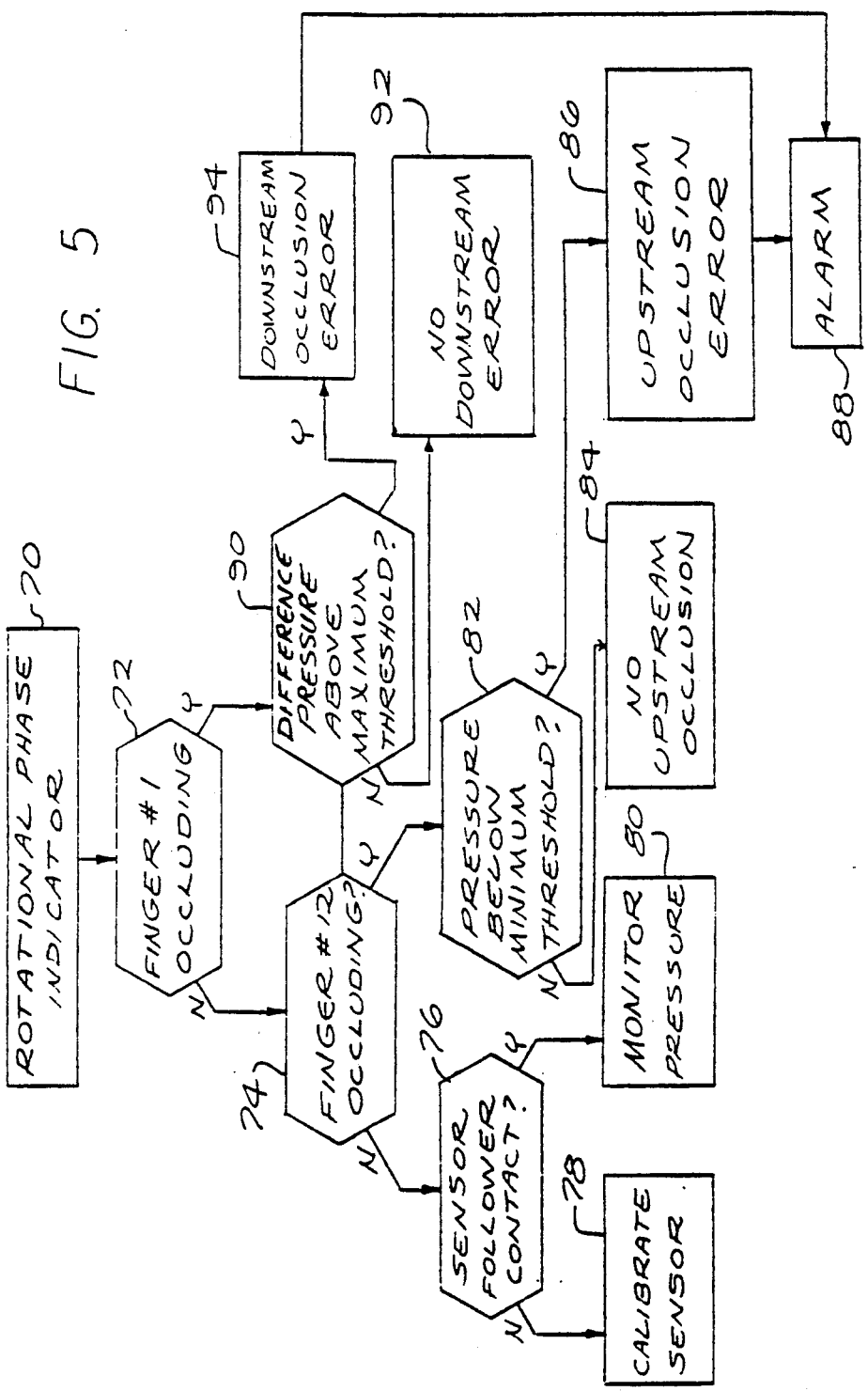

APPARATUS FOR DETECTING FLUID LINE OCCLUSION

This is a continuation-in-part of copending application Ser. No. 07/430,809 filed on Nov. 2, 1989 now abandoned.

BACKGROUND OF THE INVENTION

1. Field of the Invention

This invention relates generally to a device for detecting occlusion in a fluid line, and more particularly relates to detection of occlusion in a fluid line upstream or downstream of a peristaltic type pump used for infusion of intravenous solutions to a patient.

2. Description of Related Art

Various devices have been used for infusing intravenous fluids to a patient. In order to gain more control over the rate of fluid flow than is generally available with gravity feed IV administration sets, various types of pumps and controllers have been utilized. A peristaltic type of pump has been found to be advantageous in allowing the pumping of intravenous fluid through conventional, flexible fluid lines without fluid contact. It has been found that the operation of peristaltic pumps also allows for a wide variety of control and sensing of patency and fluid flow conditions. Important data concerning flow status can be gathered by monitoring fluid pressure changes within the intravenous fluid line.

The incorporation of a pressure sensing strain gauge assembly in a peristaltic pump in order to monitor dimensional changes in the outer diameter of an intravenous tube as an indication of fluid pressure changes in the tube in known from U.S. Pat. No. 4,690,673. In the construction of such a pressure sensing assembly, the strain gauge is attached to a strain beam which is part of an assembly mounted on a fixed mounting block to press with a generally constant displacement of the fluid line.

It would be desirable to provide an apparatus for monitoring occlusion in a fluid line upstream or downstream of a peristaltic pump mechanism, or otherwise detecting fluid pressure changes in the fluid line for detecting changes in the rate of flow due to partial closure of the line, leaks in the line, or other such problems with a pressure sensor which presses against the line with a certain degree of displacement of the fluid line only during a limited portion of the duty cycle of the pump. Such a moving pressure sensor can avoid interfering with the fluid flow during the portion of the duty cycle when the pressure sensor is not pressing against the fluid line, and would allow for periodic calibration of the pressure sensor as well. Coordination of the movement of the pressure sensor with cam follower fingers of a peristaltic pump would be desirable in order to avoid interfering with the operation of the pump, while enhancing the accuracy of pressure measurements obtained. The present invention addresses these needs.

SUMMARY OF THE INVENTION

The present invention provides an improved system for detecting pressure and occlusion in a fluid line being operated upon by a positive displacement, peristaltic pump having several cam follower fingers pressing against the fluid line sequentially to force fluid through the line peristaltically. A sensor follower finger is mounted to the cam shaft of the pump among the other peristaltic fingers in order to cyclicly press against the fluid line and displace it by a certain amount as the cam shaft rotates. The sensor follower fingers includes a strain gauge mounted on the sensor finger to generate a signal indicating the degree of force being applied by the sensor finger against the tubing, and a signal processor unit which receives this force signal determines the pressure within the fluid line based upon the signal. In an upstream mode embodiment, the signal processor compares the measured pressure to an upstream reference value and provides an occlusion alarm if the result of the comparison indicates a pressure below that reference value. In an embodiment of a downstream mode, the signal processor subtracts the measured upstream pressure from the measured downstream pressure and compares this difference pressure to a downstream reference value. In the event that the comparison indicates the difference pressure to exceed the reference value, an occlusion alarm may be provided. The force sensor is preferably a strain gauge mounted on a portion of the sensor finger which is subject to strain forces as the sensor finger presses against the tubing.

Briefly, and in general terms, an apparatus for measuring pressure within a flexible tubing being operated upon by a peristaltic pump having a plurality of cam follower fingers includes a sensor finger periodically pressing against the tubing wall with a predetermined displacement of the tubing wall without occluding the fluid line, a sensor for measuring the force exerted by the sensor finger on the tubing wall and generating a force signal indicative of the force; a signal processing unit for determining the measured pressure based upon the force signal, and for comparing the measured pressure with upstream and downstream pressure reference values during upstream and downstream modes, respectively as described above.

In a preferred embodiment, the pressure measurement apparatus includes an alarm for indicating an occlusion condition, based upon the comparison. The force sensor also preferably comprises a strain gauge mounted on a portion of the sensor finger for measuring the force exerted by the sensor finger on the tubing wall, and the strain gauge is most preferably placed within an aperture in the portion of the sensor finger which engages the tubing wall.

Other aspects and advantages of the invention will become apparent from the following detailed description and the accompanying drawings illustrating by way of example the features of the invention.

BRIEF DESCRIPTION OF THE DRAWINGS

FIG. 3 is a view similar to FIG. 1 showing the sensor follower in position during an upstream mode of the peristaltic pump;

FIG. 5 is a flow chart illustrating the operation of the signal processing unit.

DETAILED DESCRIPTION OF THE INVENTION

Figure 1:
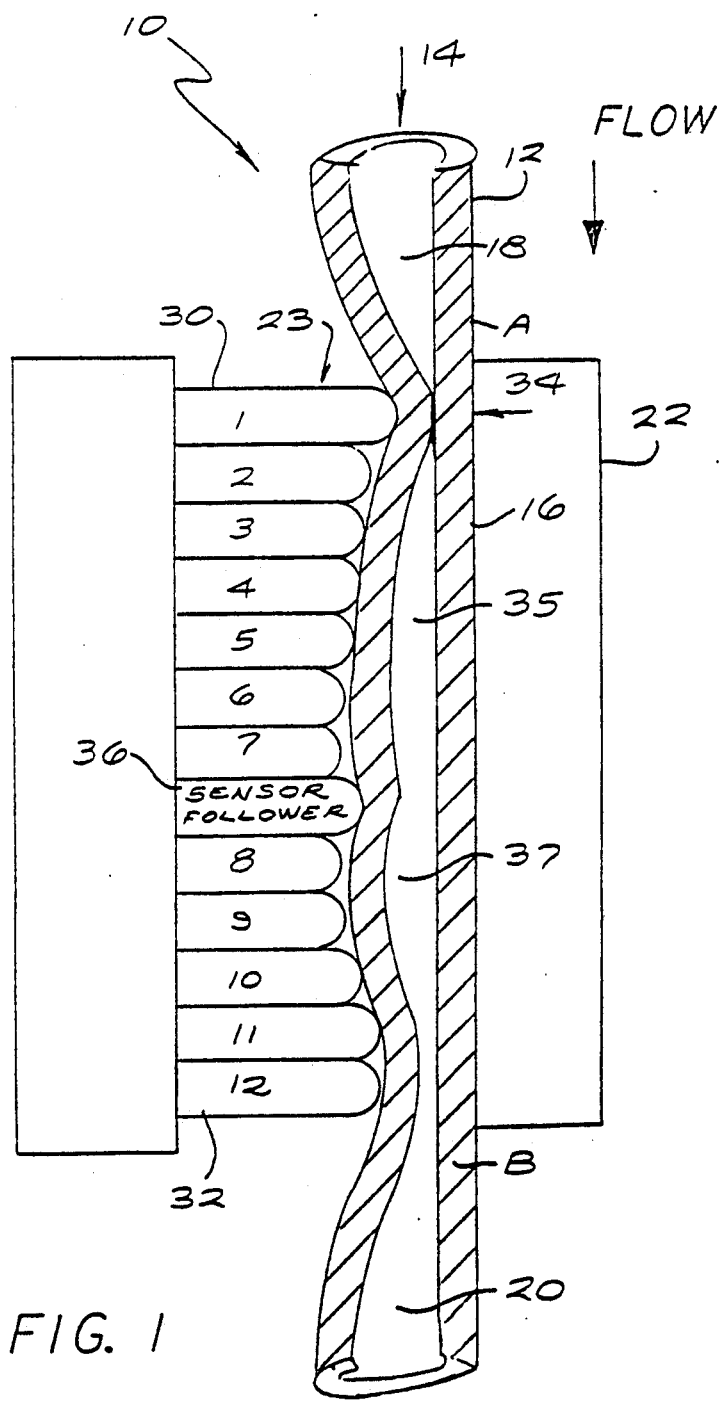
FIG. 1 is a simplified sectional view of the peristaltic finger mechanism operating upon a fluid line, and showing the placement of the sensor of the invention.

As is shown in the drawings for purposes of illustration, the invention is embodied in an apparatus and method for measuring pressure in a fluid line received in a peristaltic pump, and for determining whether the fluid line is occluded upstream or downstream of the pump mechanism. The apparatus comprises a sensor follower finger journalled to a rotating cam shaft and centrally located among a plurality of cam follower fingers journalled to the cam shaft. The sensor follower finger is adapted to press against the flexible tubing wall at a generally central portion of the segment of fluid line received in the peristaltic pump, intermediate the upstream end and downstream end cam followers. The sensor follower is adapted to cyclically press against the segment of tubing for a portion of the pump duty cycle with predetermined displacement of the tubing wall without occluding the fluid line. A sensor associated with the sensor follower finger measures the force exerted by the sensor follower finger on the tubing segment, and a signal processing unit receives the upstream and downstream pressures and determines whether occlusion has occurred upstream or downstream from the pump.

In accordance with the invention, there is therefore provided an apparatus for measuring pressure within a compressible pumping segment of a fluid line having a flexible tubing wall, including a peristaltic pump mechanism for receiving the pumping segment, the peristaltic pump mechanism having a rotating camshaft and a plurality of cam follower fingers journalled thereto and including an upstream end cam follower finger and a downstream end cam follower finger adapted to sequentially press against the pumping segment producing cyclically recurring upstream and downstream pressure communication modes of a duty cycle of the pump in which a central portion of the pumping segment is alternately in communication with only an upstream portion of the fluid line and only a downstream portion of the fluid line, respectively, the apparatus comprising a sensor follower finger journalled to the camshaft adjacent the central portion of the pumping segment and intermediate the upstream end cam follower and the downstream end cam follower, and adapted to cyclically press against the pumping segment for a portion of the duty cycle with a predetermine displacement of the tubing wall without occluding the fluid line; sensor means associated with the sensor follower finger for generating a force signal indicative of the force exerted by the sensor follower finger in pressing against the pumping segment; and signal processing means responsive to the force signal for determining a measured pressure value based upon the force signal, for comparing the measured pressure with an upstream pressure threshold value in the upstream pressure communication mode, and adapted to generate an upstream occlusion error signal when the measured pressure is less than the upstream pressure theshold value, and in a downstream pressure communication mode, for subtracting measured upstream pressure from measured downstream pressure, comparing this difference pressure to a downstream pressure threshold value and adapted to generate a downstream occlusion error signal when the measured difference pressure is greater than the downstream pressure threshold value.

The invention also provides a method for measuring pressure within a pumping segment of a fluid line having a flexible tubing wall, comprising the steps of periodically compressing the pumping segment with at least one finger member with a predetermined amount of displacement of the flexible tubing wall without occluding the fluid line; measuring a force parameter exerted by the finger member on the flexible tubing wall; generating a force signal indicating the measured force parameter; and determining fluid pressure within the tubing responsive to the force signal.

As is shown in the drawings, a peristaltic pump mechanism 10 is adapted to receive a flexible fluid tubing 12, to force fluid through the tubing in the direction of the arrow 14. The fluid tubing includes a compressible pumping segment 16 from approximately the location A to the location B, between the inlet end 18 of the tubing and the outlet end 20. Although the tubing is typically continuous, and flexible throughout its length, it is also possible that an inflexible tubing could be used, with an intermediate compressible pumping segment spliced into the inflexible tubing at the inlet and outlet ends of the compressible pumping segment, to allow a peristaltic pump mechansim to act upon the pumping segment. The peristaltic pump mechanism also includes a portion of the pump housing 22 adjacent one side of the flexible tubing, and typically several peristaltic cam follower fingers 23 journalled to a camshaft 24, which drives the peristaltic cam follower fingers to sequentially press against the flexible tubing wall of the pumping segment to force the fluid in the tubing to flow by peristaltic movement. As the cam rotates about its off center axis of rotation 26, the cam surface 28 precesses around the axis, causing the cam follower fingers to sequentially press against and move away from the tubing wall.

The farthest upstream cam follower finger 30 identified in FIG. 1 as finger No. 1 out of a sequence of 12 cam follower fingers, and the farthest downstream cam follower finger 32, identified as finger No. 12, form the outside end fingers of the peristaltic pump mechanism, and are designed to sequentially press against and occlude the fluid line, to force fluid through the tubing. In FIG. 1, the uppermost finger 30 is shown as occluding fluid tubing at the location 34, and finger No. 2, finger No. 3, finger No. 4, and so on sequentially press against the tubing and occlude the fluid flow at the area of contact, forcing fluid along the tubing. As the point of occlusion moves sequentially downstream past the central area of the cam follower fingers, the downstream portion of the fluid tubing will be sealed off from communication with the central portion of the fluid tubing, where the non-occluding sensor follower finger 36 is approximately located. At this point, fluid pressure from the upstream portion of the tubing is in fluid communication through the fluid tubing portion 35 with the tubing area adjacent the sensor follower finger. As the point of occlusion shifts to the upstream fingers, the downstream fingers culminating in finger 32 release, opening the central area adjacent the sensor follower to fluid communication with the downstream portion of the tubing 20 through the area 37 just downstream of the sensor follower. Thus, an upstream mode of communication with the central area of the tubing can be defined with relation to the point of occlusion, so that when the peristaltic point of occlusion is downstream from the sensor follower and the fluid line is opened to communication upstream of the sensor follower, the peristaltic pump mechanism is in an upstream mode of pressure communication, and when the point of occlusion is upstream of the sensor follower and the downstream portion of the tubing is open to communicate pressure to the sensor follower finger, the apparatus is in a downstream mode of pressure communication.

Figure 2:
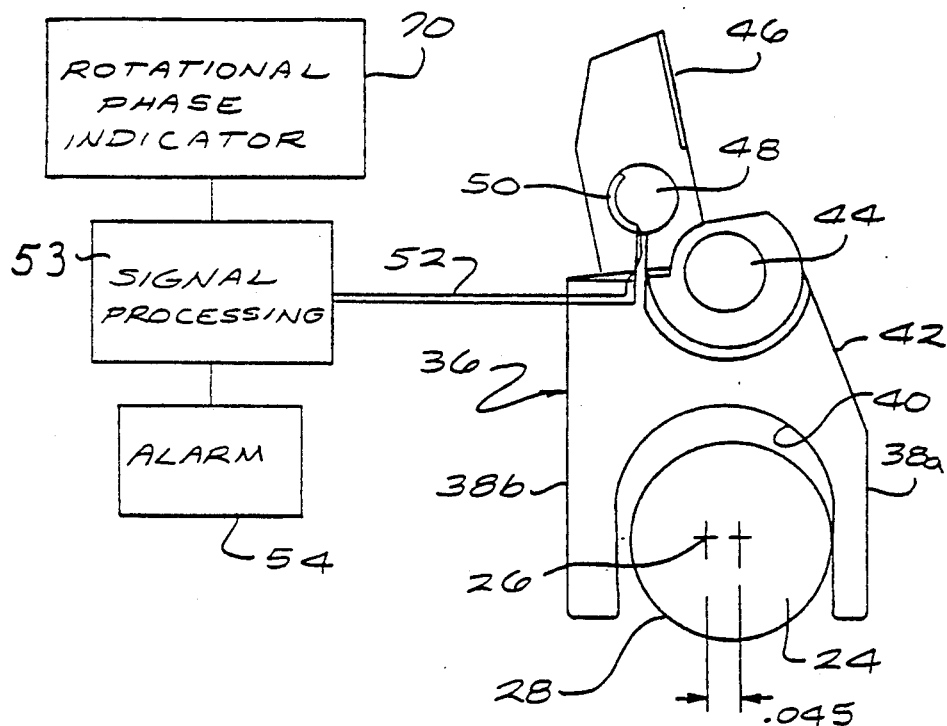
FIG. 2 is a side elevational view of a sensor follower according to the invention journalled to a cam shaft drive.

Referring to FIG. 2, the sensor follower finger 36 is generally of the same shape and construction as that of the other can follower fingers. The sensor follower finger includes cam follower arms 38a, 38b adapted to cooperate within and follow the rotation of the cam drive, and having an interior U-shaped cam follower section 40, in the main body portion 42. The sensor follower finger includes a pivot aperture 44, so that the finger can be mounted to pivot in response to the cam drive, to move the tube pressing arm 46 to press against and move away from the flexible tubing. The tube pressing arm preferably includes a protective aperture 48 containing a strain gauge mounted therein to monitor the force applied by the tube pressing arm against the flexible tubing. The strain gauge is electrically connected by the wire 52 to a signal processing unit 53, typically a microprocessor based unit or computer, which receives the force signal output from the strain gauge, and which in turn generates an occlusion error signal which may drive an alarm 54, as will be explained hereinafter.

With reference to FIGS. 1 and 3, the sensor follower finger is driven with a cam that is different from the cam sections of the other cam follower fingers, so that the sensor follower finger will not occlude the tubing, but will contact the tubing wall in order to press against the wall with a limited displacement of the tubing wall. Furthermore, the cam for this sensor follower finger is preferably formed so that if the follower No. 2 is occluding the tubing, the sensor follower will be in contact with and pressing against the tubing, so that if the tubing is occluded downstream the sensor will reflect the occlusion in the output force signal. When the farthest downstream follower No. 12 occludes the tubing the sensor follower will again be in contact with the tubing so that if, for example, an upstream roller clamp is closed, a negative pressure will occur, which will result in a vacuum within the compressible segment of the tubing, the tubing will collapse, and the sensor follower will indicate an upstream occlusion.

With reference to FIG. 3, it can be seen that when the point of occlusion 55 is at about the location of the farthest downstream finger No. 12, the portion of the fluid line upstream 56 of the fluid line is in pressure communication with the sensor follower finger, and the downstream portion of the fluid line 58 is closed off. A vacuum 60 created by upstream occlusion, such as a roller clamp on the fluid line being closed, or some other blockage in the line would allow a vacuum to build up within the compressible pumping segment as the fluid is forced downstream by the peristaltic pump mechanism.

Figure 4:
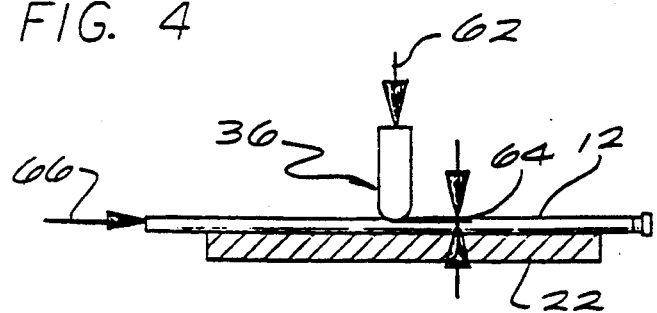
FIG. 4 is a schematic diagram of the relationship of the sensor follower to flexible tubing within the peristaltic pump.

In the following discussion of determination of fluid line pressure based upon displacement of a portion of flexible tubing by a sensor follower arm and the measured force applied by the arm on the tubing, reference is made to the simplified schematic diagram shown in FIG. 4. A non-occluding sensor follower arm or blade 36 is sown as being directed against the fluid line 12 with a degree of force (in grams) and in a direction indicated by the vector 62. The blade displacement 64 of the tubing wall is in opposition to the applied pressure 66 within the fluid.

Accurate correlation between blade force against tubing (sensor response) and tubing internal pressure was found to require the use of a substantial blade displacement value, ideally in the range of from 50 to 70 mils. However, an excessive displacement should not restrict flow within the tubing. Force relaxation and load hysteresis tests further show the tube stiffness characteristics to be significantly time dependent, so that accurate correlations between sensor response and tubing internal pressure in practice should allow for execution of a frequent tubing calibration routine with actual operating flow rates and operating temperatures. Zeroing of the sensor follower finger force measurement is made possible by movement of the sensor follower finger away from the tubing wall during a portion of the duty cycle of the peristaltic pump.

Tests performed with various tubing vacuum levels simulating an upstream occlusion condition showed fairly linear results for blade force versus displacement, and internal vacuum levels in the tubing ranging from 0 to about 5 psig vacuum. At a vacuum level of about 7.5 psig, blade force levels fall off dramatically. Typically somewhere between 7.5 psig and 10 psig vacuum levels, the tube completely buckles or collapses under the action of the internal vacuum. In this state, the tubing wall becomes completely flattened and loses contact all together with the sensor follower blade.

In the operation of the signal processing unit, generally described in the flow chart shown in FIG. 5, the signal processing unit ideally receives input from a rotational phase indicator 70, which may take the form of an optical flag assembly which interrupts a photoelectric beam, either in conjunction with the cam drive itself or a motor (not shown) which drives the rotation of the cam shaft. With a signal from the rotational phase indicator, the signal processor can identify which of the cam follower fingers is occluding the fluid line at any given moment during the duty cycle of the pump. A determination is made at 72 whether the most upstream cam follower finger is occluding the fluid line. If it is not, the same decision is made at 74 concerning the most downstream cam follower finger, finger No. 12. If finger No. 12 is not occluding the tubing, a determination is made at 76 as to whether the sensor follower is contacting the tubing, and if it is not, since the strain gauge will then be generating a signal which correlates with zero pressure, a calibration of the sensor at 78 can be made. Otherwise, if the sensor follower is contacting the tubing, the fluid pressure can be monitored at 80. When finger No. 12 is occluding the fluid line, a determination can be made at 82 whether the measured pressure determined by the signal processing unit is below a minimum threshold. A typical minimum pressure threshold would be zero, so that if the pressure level were determined to be above this level, at 84, there would not be the indicated upstream occlusion, and if a pressure less than zero were detected, this would give an indication at 86 of an upstream occlusion error condition, which may also result in an alarm signal to the alarm 88. Similarly, if it is determined that finger No. 1 is occluding the fluid line, it can be determined at 90 whether a measured pressure difference between the downstream and upstream measured pressures is above a maximum threshold. If the measured pressure difference is less than the maximum pressure threshold, such as for example 10 psig, then the determination at 92 would be that no downstream occlusion exists. Otherwise, if the measured pressure difference were above this maximum threshold, the signal processing unit would generate a downstream occlusion error signal, and the signal processing unit may also generate an alarm signal to activate the alarm 88.

Although an embodiment is discussed above where a pressure difference between measured downstream and upstream pressures is used to determine if an occlusion exists, other embodiments may be possible. For example, the measured downstream pressure alone may be compared to a threshold to determine the existence or nonexistence of a downstream occlusion.

In view of the foregoing, it has been demonstrated that the system of the invention for measuring pressure within the fluid line can be used for detecting occlusion within the fluid line either upstream or downstream from a peristaltic pump mechanism operating on the fluid line. It is also significant that the sensor follower finger is adapted for movement correlated with that of the other cam follower fingers in order to avoid restriction of fluid flow, and to allow periodic calibration of the sensor.

Although specific embodiments of the invention have been described and illustrated, it is clear that the invention is susceptible to numerous modifications and adaptations within the ability of those skilled in the art and without the exercise of the inventive faculty. Thus, it should be understood that various changes in form, detail and use of the present invention may be made without departing from the spirit and scope of this invention.

We claim:

1. An apparatus for measuring pressure within a compressible pumping segment of a fluid line having a flexible tubing wall, including a peristaltic pump mechanism for receiving said pumping segment, said peristaltic pump mechanism having a rotating camshaft and a plurality of cam follower fingers journalled thereto and including an upstream end cam follower finger and a downstream end cam follower finger adapted to sequentially press against said pumping segment producing cyclically recurring upstream and downstream pressure communication modes of a duty cycle of said pump mechanism in which a central portion of said pumping segment is alternately in communication with only an upstream portion of said fluid line and only a downstream portion of said fluid line, respectively, said apparatus comprising:

a sensor follower finger journalled to said camshaft adjacent said central portion of said pumping segment and intermediate said upstream end cam follower finger and said downstream end cam follower finger, and adapted to cyclically press against said pumping segment for a portion of said duty cycle with a predetermined displacement of said tubing wall without occluding said fluid line;

sensor means associated with said sensor follower finger for generating a force signal indicative of said force exerted by said sensor follower finger in pressing against said pumping segment; and signal processing means responsive to said force signal for determining a measured pressure value based upon said force signal, for comparing said measured pressure with an upstream pressure threshold value in said upstream pressure communication mode and adapted to generate an upstream occlusion error signal when said measured pressure is less than said upstream pressure threshold value, and for subtracting said measured pressure in said downstream pressure communication mode from an upstream measured pressure to result in a difference pressure and adapted to generate a downstream occlusion error signal when said difference pressure is greater than a downstream pressure threshold value.

2. The apparatus of claim 1, further including alarm means for indicating an occlusion condition responsive to said upstream and downstream occlusion error signals.

3. The apparatus of claim 1, wherein said sensor follower finger has a tubing wall engaging end, a cam engaging end, and an intermediate pivot point therebetween, and said sensor means for generating the force signal comprises a strain gauge mounted on said sensor finger for measuring the force exerted by said sensor finger against said tubing wall.

4. The apparatus of claim 3, wherein said tubing wall engaging end includes an aperture, and said strain gauge is mounted to said sensor finger within said aperture.

5. The apparatus of claim 1 wherein the signal processor means is calibrated to the sensor means during the part of the cycle when the sensor follower finger is not in contact with the pumping segment.

6. The apparatus of claim 5 wherein the signal processor means is calibrated to the sensor means during each cycle of the sensor follower finger during the part of the cycle when the sensor follower finger is not in contact with the pumping segment.

7. The apparatus of claim 1 wherein the sensor means has a zero force value and the signal processor means is calibrated to this zero force value during the part of the cycle when the sensor follower finger is not in contact with the pumping segment.

8. The apparatus of claim 7 wherein the sensor means has a zero force value and the signal processor means is calibrated to this zero force value during each cycle of the sensor follower finger during the part of the cycle when the sensor follower finger is not in contact with the pumping segment.

9. A method for measuring pressure within a compressible pumping segment of a fluid line having a flexible tubing wall, said pumping segment being received in a peristaltic pump mechanism, said peristaltic pump mechanism having a rotating camshaft and a plurality of cam follower fingers journalled thereto and including an upstream end cam follower finger and a downstream end cam follower finger adapted to sequentially press against said pumping segment producing cyclically recurring upstream and downstream pressure communication modes of a duty cycle of said pump mechanism in which a central portion of said pumping segment is alternately in communication with only an upstream portion of said fluid line and only a downstream portion of said fluid line, respectively, comprising the steps of:

periodically compressing said pumping segment with at least one finger member with a predetermined amount of displacement of said flexible tubing wall without occluding said fluid line;

measuring a force parameter exerted by said finger member on said flexible tubing wall and generating a force signal indicating said measured force parameter; and determining fluid pressure within said tubing responsive to said force signal.

10. The method of claim 9, wherein said pressure is determined from said force parameter, said amount of displacement, and a tube stiffness constant based upon the modulus of elasticity and thickness of the tubing wall.

11. The method of claim 9, wherein said displacement is in the range of from about 50 mils. to about 70 mils.

12. The method of claim 9 wherein:
the step of measuring a force parameter comprises applying a gauge to the at least one finger member to measure said force parameter; and
the step of determining fluid pressure comprises the step of calibrating the gauge during the part of the cycle when the at least one finger member is not compressing said tubing wall.

13. The method of claim 12 wherein the step of calibrating during the part of the cycle when the at least one finger member is not compressing said tubing wall comprising calibrating the gauge during each cycle.

14. The method of claim 9 wherein:
the step of measuring a force parameter comprises applying a gauge to the at least one finger member to measure said force parameter, said gauge having a zero force value; and
the step of determining fluid pressure comprises the step of calibrating to this zero force value during the part of the cycle when the at least one finger member is not compressing the tubing wall.

15. The method of claim 14 wherein the step of calibrating to the zero force value includes calibrating to the zero force value during each cycle of the sensor follower finger during the part of the cycle when the sensor follower finger is not compressing the pumping segment.

16. The method of claim 9 wherein said step of determining fluid pressure comprises:
determining upstream fluid pressure by receiving said measured force parameter during an upstream pressure communication mode;
determining downstream fluid pressure by receiving said measured force parameter during an upstream pressure communication mode and by receiving said measured force parameter during a downstream pressure communication mode and subtracting said upstream measured force parameter from said downstream measured force parameter.

17. The method of claim 16 further comprising the steps of:
comparing the upstream fluid pressure to a predetermined upstream pressure threshold and providing an occlusion signal in the event that the upstream fluid pressure is less than said threshold;
comparing the downstream fluid pressure to a predetermined downstream pressure threshold and providing an occlusion signal in the event that the downstream fluid pressure is greater than said threshold.

18. An apparatus for measuring pressure within a fluid line having a pumping segment with a flexible tubing wall, including a peristaltic pump mechanism for receiving said pumping segment, said peristaltic pump mechanism having a plurality of peristaltic fingers including an upstream end finger and a downstream end finger adapted to sequentially press against said pumping segment producing cyclically recurring upstream and downstream pressure communication modes of a duty cycle of said pump mechanism in which a portion of said pumping segment between said end fingers is alternately in communication with only an upstream portion of said fluid line and only a downstream portion of said fluid line respectively, said apparatus comprising:
a sensor follower finger disposed between said upstream end finger and said downstream end finger, adapted to cyclically press against said pumping segment for a portion of said duty cycle to displace the tubing wall of said segment by a predetermined amount;
a sensing gauge coupled to said sensor follower finger for generating a force signal indicative of the force exerted by said sensor follower finger in pressing against said tubing wall; and
a processor for receiving said force signal in said upstream pressure communication mode and for receiving said force signal in said downstream pressure communication mode and adapted to generate an occlusion signal based on the values of said force signals.

19. The apparatus of claim 18 wherein the processor is calibrated to the sensing gauge during the part of the cycle when the sensor follower finger is not in contact with the tubing wall.

20. The apparatus of claim 19 wherein the processor is calibrated to the sensing gauge during each cycle of the sensor follower finger during the part of the cycle when the sensor follower finger is not in contact with the tubing wall.

21. The apparatus of claim 18 wherein the gauge has a zero force value and the processor is calibrated to this zero force value during the part of the cycle when the sensor follower finger is not in contact with the tubing wall.

22. The apparatus of claim 21 wherein the gauge has a zero force value and the processor is calibrated to this zero force value during each cycle of the sensor follower finger during the part of the cycle when the sensor follower finger is not in contact with the tubing wall.

23. An apparatus for measuring pressure within a compressible pumping segment of a fluid line having a flexible tubing wall, including a peristaltic pump mechanism for receiving said pumping segment, said peristaltic pump mechanism having a rotating camshaft and a plurality of cam follower fingers journalled thereto and including an upstream end cam follower finger and a downstream end cam follower finger, said plurality of cam follower fingers adapted to sequentially press against said pumping segment producing cyclically recurring upstream and downstream pressure communication modes of a duty cycle of said pump mechanism in which a portion of said pumping segment disposed between said upstream end and downstream end cam follower fingers is alternately in communication with only an upstream portion of said fluid line and only a downstream portion of said fluid line, respectively, said apparatus comprising:
a sensor follower finger journalled to said camshaft adjacent said portion of said pumping segment and intermediate said upstream end cam follower finger and said downstream end cam follower finger, and adapted to cyclically press against said pumping segment for a portion of said duty cycle to displace said tubing wall by a predetermined amount;
sensor means associated with said sensor follower finger for generating a force signal indicative of said force exerted by said sensor follower finger in pressing against said pumping segment; and a signal processor responsive to said force signal for determining a measured pressure value based upon said force signal, for comparing said measured pressure with an upstream pressure threshold value in said upstream pressure communication mode and adapted to generate an upstream occlusion error signal when said measured pressure is less than said upstream pressure threshold value, and for subtracting said measured pressure in said downstream pressure communication mode from an upstream measured pressure to result in a difference pressure and adapted to generate a downstream occlusion error signal when said difference pressure is greater than a downstream pressure threshold value.

24. The apparatus of claim 23 further including alarm means for indicating an occlusion condition responsive to said upstream and downstream occlusion error signals.

25. The apparatus of claim 23 wherein said sensor follower finger has a tubing wall engaging end, a cam engaging end, and an intermediate pivot point therebetween, and the sensor means comprises a strain gauge mounted on said sensor finger for measuring the force exerted by said sensor finger against said tubing wall.

26. The apparatus of claim 23 wherein the processor is calibrated to the sensor means during each cycle of the sensor follower finger during the part of the cycle when the sensor follower finger is not in contact with the tubing wall.

27. The apparatus of claim 25 wherein the gauge has a zero force value and the processor is calibrated to this zero force value during each cycle of the sensor follower finger during the part of the cycle when the sensor follower finger is not in contact with the tubing wall.

28. An apparatus for measuring pressure within a compressible pumping segment of a fluid line having a flexible tubing wall, including a peristaltic pump mechanism for receiving said pumping segment, said peristaltic pump mechanism having a rotating camshaft and a plurality of cam follower fingers journalled thereto and including an upstream end cam follower finger and a downstream end cam follower finger adapted to sequentially press against said pumping segment producing cyclically recurring upstream and downstream pressure communication modes of a duty cycle of said pump mechanism in which an intermediate portion of said pumping segment disposed between said upstream and downstream cam follower fingers is alternately in communication with only an upstream portion of said fluid line and only a downstream portion of said fluid line, said apparatus comprising:

a sensor follower finger journalled to said camshaft and adapted to cyclically press against said intermediate pumping segment for a portion of said duty cycle to displace said tubing wall by a predetermined amount;

sensor means associated with said sensor follower finger for generating a force signal indicative of said force exerted by said sensor follower finger in pressing against said pumping segment; and a signal processor responsive to said force signal for determining a measured pressure value based upon said force signal; and in said upstream pressure communication mode, for comparing said measured pressure value with an upstream pressure threshold value and adapted to generate an upstream occlusion error signal when said measured pressure is less than said upstream pressure threshold value; and in said downstream pressure communication mode, for subtracting said upstream measured pressure value from said downstream measured pressure value and comparing said measured pressure difference with a downstream pressure reference value and adapted to generate a downstream occlusion error signal when said measured pressure is greater than said downstream pressure threshold value.

29. The apparatus of claim 28 further including alarm means for indicating an occlusion condition responsive to said upstream and downstream occlusion error signals.

30. The apparatus of claim 28 wherein said sensor follower finger has a tubing wall engaging end, a cam engaging end, and an intermediate pivot point therebetween, and the sensor means comprises a strain gauge mounted on said sensor finger for measuring the force exerted by said sensor finger against said tubing wall.

31. The apparatus of claim 28 wherein the processor is calibrated to the sensor means during each cycle of the sensor follower finger during the part of the cycle when the sensor follower finger is not in contact with the tubing wall.

32. The apparatus of claim 28 wherein the sensor means has a zero force value and the processor is calibrated to this zero force value during each cycle of the sensor follower finger during the part of the cycle when the sensor follower finger is not in contact with the tubing wall.

* * * * *